US011977017B2

(12) United States Patent
Sanchez-Martin et al.

(10) Patent No.: US 11,977,017 B2
(45) Date of Patent: May 7, 2024

(54) AUTOMATED CONFIGURATION OF FLOW CYTOMETRY MACHINES

(71) Applicant: International Business Machines Corporation, Armonk, NY (US)

(72) Inventors: Marta Sanchez-Martin, Somerville, MA (US); Claudia S. Huettner, Jamaica Plain, MA (US); Jia Xu, Somerville, MA (US); Cheryl L Eifert, Watertown, MA (US); Elinor Dehan, Haniel (IL); Shang Xue, Cambridge, MA (US); Vanessa Michelini, Boca Raton, FL (US)

(73) Assignee: International Business Machines Corporation, Armonk, NY (US)

( * ) Notice: Subject to any disclaimer, the term of this patent is extended or adjusted under 35 U.S.C. 154(b) by 1155 days.

(21) Appl. No.: 16/254,958

(22) Filed: Jan. 23, 2019

(65) Prior Publication Data
US 2020/0232901 A1    Jul. 23, 2020

(51) Int. Cl.
*G01N 15/10*    (2024.01)
*G01N 15/01*    (2024.01)
(Continued)

(52) U.S. Cl.
CPC ......... *G01N 15/1012* (2013.01); *G06F 30/27* (2020.01); *G16B 40/00* (2019.02);
(Continued)

(58) Field of Classification Search
CPC .......... G01N 15/1012; G01N 15/1459; G01N 2015/0065; G01N 2015/1006
(Continued)

(56) References Cited

U.S. PATENT DOCUMENTS 5,093,234 A    3/1992 Schwartz
5,314,824 A    5/1994 Schwartz
(Continued)

OTHER PUBLICATIONS

Sony Biotechnology Inc, "SH800S Cell Sorter: Automation from Set-up to Analysis." [Accessed Jul. 10, 2018] https://www.sonybiotechnology.com/us/instruments/sh800s-cell-sorter/system-sh800s.

(Continued)

*Primary Examiner* — Michael McCullough
*Assistant Examiner* — Molly K Devine
(74) *Attorney, Agent, or Firm* — Edell, Shapiro & Finnan, LLC

(57) ABSTRACT

Computer based methods, systems, and computer readable media are provided for intelligently sorting cells using machine learning. A biological cell analysis sorting machine, wherein the biological cell analysis sorting machine comprises a flow cytometry system and a cell analytics sorting system, may be configured to detect configuration issues by analyzing results of a sorting experiment performed by the biological cell analysis sorting machine. An analysis of a history of prior sorting experiments and associated configuration settings may be performed and a corpus of documents pertaining to the sorting experiment based on the detected configuration issues may be analyzed. Updated configuration settings for the biological cell analysis sorting machine based on the performed analysis may be determined, and the biological cell analysis sorting machine may be configured with the updated configuration settings to conduct a desired sorting experiment.

14 Claims, 5 Drawing Sheets

(51) Int. Cl.
  *G01N 15/14* (2024.01)
  *G01N 15/149* (2024.01)
  *G06F 30/27* (2020.01)
  *G16B 40/00* (2019.01)
  *G16B 40/20* (2019.01)
  *G16C 20/70* (2019.01)
  *H04L 67/01* (2022.01)

(52) U.S. Cl.
  CPC ............ *G16B 40/20* (2019.02); *G16C 20/70* (2019.02); *G01N 15/01* (2024.01); *G01N 2015/1006* (2013.01); *G01N 15/1459* (2013.01); *G01N 15/149* (2024.01); *H04L 67/01* (2022.05)

(58) Field of Classification Search
  USPC .......................................................... 702/85
  See application file for complete search history.

(56) References Cited

U.S. PATENT DOCUMENTS

| | | | |
|---|---|---|---|
| 6,897,954 | B2 | 5/2005 | Bishop et al. |
| 6,941,005 | B2* | 9/2005 | Lary .................. G01N 15/1425 382/133 |
| 9,965,702 | B1* | 5/2018 | Angeletti ........... G01N 15/1429 |
| 2013/0051650 | A1* | 2/2013 | Santamaria-Pang ... G16B 40/20 382/133 |
| 2014/0097129 | A1* | 4/2014 | Foster ................ G01N 15/1459 209/579 |
| 2014/0120570 | A1* | 5/2014 | Yu ............................ G01N 1/34 210/695 |
| 2016/0169786 | A1* | 6/2016 | Albitar ................. G06K 9/6282 702/19 |
| 2017/0102310 | A1* | 4/2017 | Xu ......................... G01N 15/06 |
| 2018/0247195 | A1* | 8/2018 | Kumar ..................... G06N 3/08 |

OTHER PUBLICATIONS

Sony Biotechnology Inc, "SH800S Cell Sorter, Software." [Accessed Jul. 10, 2018] https://www.sonybiotechnology.com/us/instruments/sh800s-cell-sorter/software.

J. Yu, "CellSort: a support vector machine tool for optimizing fluorescence-activated cell sorting and reducing experimental effort," Bioinformatics, vol. 33, Issue 6, Mar. 15, 2017, pp. 909-916.

M. Thomas (2018), "Quantifying cell densities and biovolumes of phytoplankton communities and functional groups using scanning flow cytometry, machine learning and unsupervised clustering." PLoS ONE 13(5): e0196225. https://doi.org/10.1371/journal.pone.0196225.

A. Cossarizza, "Guidelines for the use of flow cytometry and cell sorting in immunological studies," Eur. J. Immunol. 2017. 47: 1584-1797.

G. Lee, "Machine Learning for Flow Cytometry Data Analysis." Ph.D. Dissertation (Electrical Engineering: Systems), University of Michigan, 2011.

* cited by examiner

AUTOMATED CONFIGURATION OF FLOW CYTOMETRY MACHINES

1. TECHNICAL FIELD

Present invention embodiments relate to automation of flow cytometry machines, and more specifically, to automating configuration of flow cytometry machines to improve cell throughput and cell classification.

2. DISCUSSION OF THE RELATED ART

Immunophenotyping is a complex laboratory technique in which cells are imaged and studied based on size, complexity, and often, specific biomarkers. This technique is broadly used in research and clinical settings of biomedical fields. In the clinic, immunophenotyping is fundamental for the accurate diagnosis of patients with blood cancers or other diseases. In the research laboratory, immunophenotyping helps differentiate between different types of cells, and may be useful for generating research models for investigating the effects of different treatments as well as designing novel immunotherapies.

Immunophenotyping may also be used in flow cytometry to identify and sort different types of cells. For example, cells may be labeled using a fluorescently labeled antibody, and subjected to cell sorting by placing the cells in a fluid stream in which the cells move past a set of detectors. In this approach, the principal investigator manually sets up the sorting experiment, configuring voltages, flow rates, and gates to collect cells based on identification of cell populations of interest, without receiving corrections or feedback from the flow cytometry device as the sorting experiment progresses.

SUMMARY

According to embodiments of the present invention, methods, systems and computer readable media are provided for intelligently sorting cells using a biological cell analysis sorting machine, wherein the biological cell analysis sorting machine comprises a flow cytometry system and a cell analytics sorting system that sorts cells. The cell analysis sorting machine may be configured to detect configuration issues by analyzing results of a sorting experiment performed by the biological cell analysis sorting machine. An analysis of a history of prior sorting experiments and associated configuration settings may be performed and a corpus of documents pertaining to the sorting experiment based on the detected configuration issues may be analyzed. Updated configuration settings for the biological cell analysis sorting machine based on the performed analysis may be determined, and the biological cell analysis sorting machine may be configured with the updated configuration settings to conduct a desired sorting experiment. Accordingly, the present techniques may be used to automate aspects of flow cytometry, namely selection of flow cytometry configuration settings. Flow cytometry configuration settings have traditionally been selected by a user in a heuristic manner. Accordingly, reproducibility of cell sorting is often challenging. Present techniques, by automating selection of configuration settings, may help standardize and optimize configuration settings for a flow cytometry system. Additionally, existing flow cytometry systems do not learn from historical sorting experiments to provide feedback in order to improve future sorting experiments.

Typically, configuration settings include one or more of a flow rate, various voltages, and gates. In some cases, configuration settings may also include a type of flow cytometry device or machine. Accordingly, automated selection of specific configuration settings allows cell sorting experiments to become more standardized and reproducible.

In one aspect, updated configuration settings may be determined using a machine learning system, wherein the machine learning system is trained using configuration settings and optionally other information from prior sorting experiments. Thus, machine learning techniques may be used to select configuration settings to automatically configure a flow cytometer.

In another aspect, cell sorting results are evaluated based upon a determined experimental error. The experimental error is provided as feedback to the biological cell analysis sorting machine, and the configuration settings are modified automatically to reduce the experimental error. In this case, real-time or near real-time evaluation of experimental error may be performed to provide feedback to the biological cell analysis sorting machine to modify configuration settings to improve cell sorting results. Present techniques may evaluate cell sorting results of the biological cell analysis sorting machine in order to optimize configuration settings.

Optionally, the configuration settings are selected based upon a cell type. This allows specific configuration settings to be associated with specific cell types to optimize cell sorting in a cell-specific manner.

Typically, a ranked list of updated configuration settings is provided by the biological cell analysis sorting machine. An updated configuration setting from the ranked list may be implemented by the flow cytometry system. When a desired cell sorting efficiency is not achieved, an alternative updated configuration setting of the ranked list may be implemented until the desired cell sorting efficiency is achieved. The system, by generating the ranked list, may predict optimal or near optimal configuration settings for cell sorting.

Optionally, the biological cell analysis sorting machine is configured to sort cells based on the presence of two to six biomarkers. Traditionally, separation of cells with high complexity is challenging and difficult to replicate. Present techniques help to ensure reproducibility and may help optimize configuration settings for complex sorting experiments.

Historical data may comprise flow cytometry sorting experiments and associated configuration settings from one or more resources including but not limited to scientific literature, lab protocols, academic institutions, research institutions, and previously conducted sorting experiments by the flow cytometry system. The system may consider configuration settings from a variety of resources in order to predict optimal configuration settings (or at least to improve sorting results) for a given flow cytometry system.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

DETAILED DESCRIPTION

Methods, systems, and computer readable media are provided to automate and improve cell sorting using a biological cell sorting analysis machine. The machine may also utilize machine learning to select and adjust configuration settings prior to and during cell sorting to improve results.

Currently, flow cytometry devices, including fluorescence-activated cell sorting (FACS) devices, are pre-configured for each sorting experiment. Typically, such configuration is performed manually by personnel having training and expertise in flow cytometry. Determining the configuration settings is a time consuming and complex process, which may vary from one flow cytometry machine to another making reproducibility between machines difficult.

For given cell types and/or types of cell sorting experiments, present techniques may employ machine learning to automatically select flow cytometry (including FACS) configuration settings, configure the flow cytometry system, and monitor and update flow cytometry configuration settings during the process of cell sorting, without human intervention, to improve or optimize experimental results. Thus, these techniques may be applied to automate and adapt the configuration of biological cell analysis sorting machines at setup and during cell sorting. Historical data from previous experiments may be analyzed and used to automatically configure the biological cell analysis sorting machine for a desired cell sorting experiment.

Figure 1:
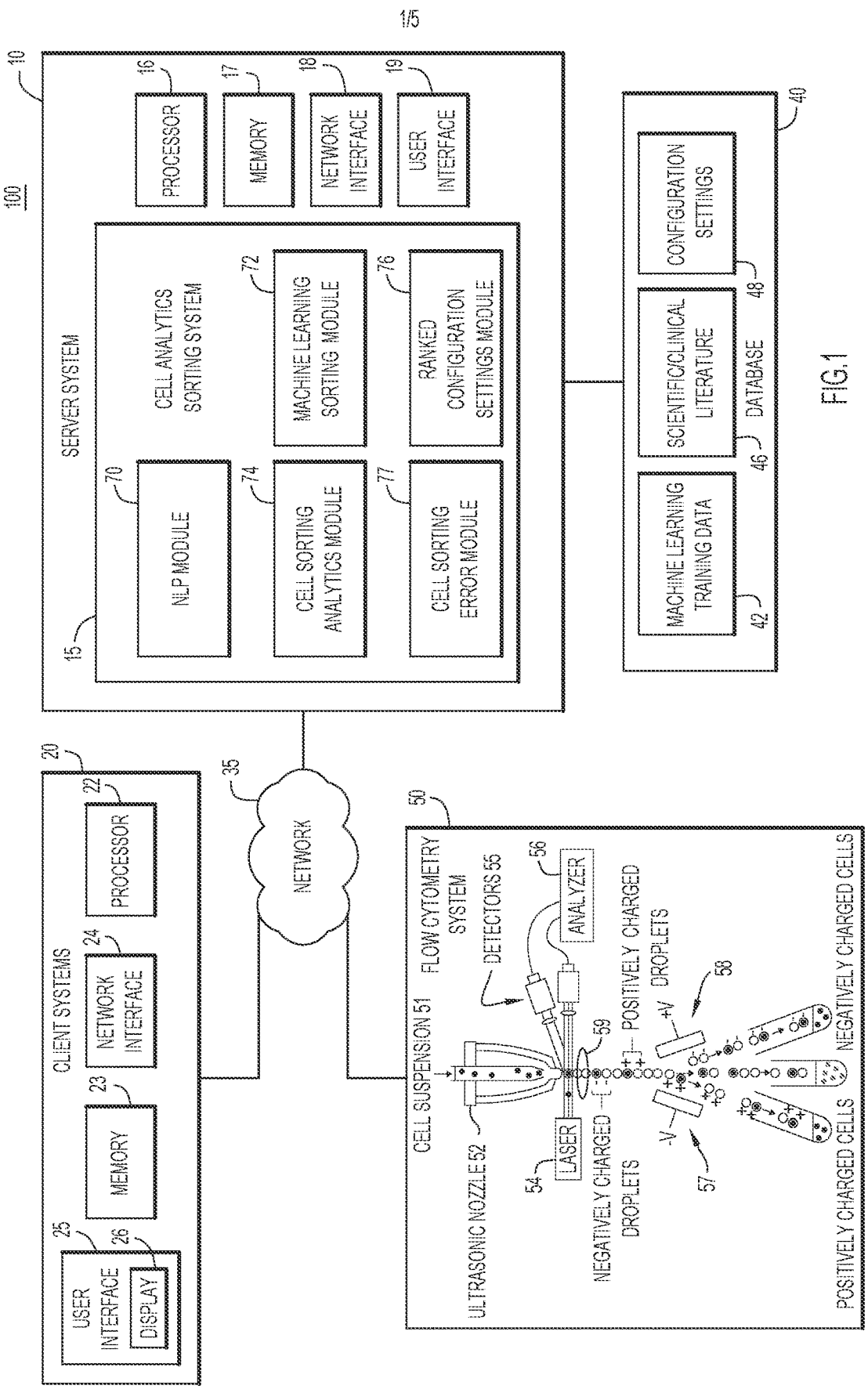
FIG. 1 is a block diagram of an example computing environment for the biological cell analysis sorting machine, according to embodiments of the present disclosure.

An example environment 100 for use with present invention embodiments is illustrated in FIG. 1. Specifically, the environment includes one or more server systems 10, and one or more client or end-user systems 20. Server systems 10 and client systems 20 may be remote from each other and communicate over a network 35. Server systems 10 may be connected to the flow cytometry system 50 through network 35, or alternatively, server systems 10 may be integrated with flow cytometry system 50. The network may be implemented by any number of any suitable communications media (e.g., wide area network (WAN), local area network (LAN), Internet, Intranet, etc.). Alternatively, server systems 10 and client systems 20 may be local to each other, and communicate via any appropriate local communication medium (e.g., local area network (LAN), hardwire, wireless link, Intranet, etc.).

Client systems 20 enable users to submit inputs to a cell analytics sorting system 15 (e.g., types of cells, type of sorting experiment, fluorescent labels, etc.) of server systems 10 to control the flow cytometry system 50. The client systems may present a graphical user (e.g., GUI, etc.) or other interface (e.g., command line prompts, menu screens, etc.) to solicit information from users pertaining to the desired analysis, and may provide reports including analysis results (e.g., suggested flow cytometry/FACS configuration settings, results of cell sorting, error, ranked configuration settings, etc.).

A database system 40 may store various information for the analysis (e.g., machine learning training data 42, scientific clinical literature 46, configuration settings 48, etc.). The database system 40 may be implemented by any conventional or other database or storage unit, may be local to or remote from server systems 10 and client systems 20, and may communicate via any appropriate communication medium (e.g., local area network (LAN), wide area network (WAN), Internet, hardwire, wireless link, Intranet, etc.).

Server systems 10 and client systems 20 may be implemented by any conventional or other computer systems preferably equipped with a display or monitor, a base (e.g., including at least one processor 16, 22, one or more memories 17, 23 and/or internal or external network interfaces or communications devices 18, 24 (e.g., modem, network cards, etc.)), optional input devices (e.g., a keyboard, mouse or other input device) as part of a user interface 19, 25 and a display 26, and any commercially available and custom software (e.g., server/communications software, cell analytics sorting system 15, browser/interface software, etc.).

Alternatively, one or more client systems 20 may automate operation of the flow cytometry system 50, when operating as a stand-alone unit. In a stand-alone mode of operation, the client system stores or has access to the data (e.g., machine learning training data 42, scientific/clinical literature 46, configuration settings 48, etc.), and includes a cell analytics sorting system 15 to control the flow cytometry system 50. The graphical user (e.g., GUI, etc.) or other interface (e.g., command line prompts, menu screens, etc.) solicits information from a corresponding user pertaining to the desired analysis, and may provide reports including analysis results (e.g., suggested flow cytometry/FACS configuration settings, results of cell sorting, error, ranked configuration settings, etc.).

Machine learning training data 42 may include configuration settings from previous flow cytometry experiments, adjusted and compensated for different types of cell separation experiments and different cell types, as well as configuration settings extracted from published scientific/clinical literature 46 (e.g., scientific publications, clinical documents, laboratory protocols, and documents from other FACS facilities (e.g., clinical facilities and hospitals, companies, research institutions and academic centers using flow cytometry, etc.)). Cell samples from commercially available sources, academic research institutions, clinical facility sources, etc. may be sorted using the techniques provided herein. Additionally, sorting experiments performed by the flow cytometry system 50 may generate additional machine learning training data sets, which may be stored in machine learning training data 42, and used to update the trained machine learning sorting module 72, both prior to sorting operations and during sorting operations, to further improve results of sorting experiments. Machine learning training data may include feature sets extracted from scientific/clinical literature 46 and configuration settings 48 (e.g., configuration settings determined from sorting experiments performed by flow cytometry system 50) for training the machine learning sorting module 72. In some cases, training data may include data from sorting experiments performed on mammalian cells (e.g., mouse, human, etc.) or other types of cells.

The cell analytics sorting system, once trained, may provide feedback on experimental configuration settings to detect potential issues when analyzing a given flow cytometry setup. For example, the present system may analyze results of sorting experiments (e.g., from scientific/clinical literature 46 and other information including configuration settings 48), based on presence and frequency of different cell populations to indicate configuration issues, and may provide alternative configurations for improving sorting of the different cell populations. In some aspects, the system is trained to automatically configure and set up photomultiplier tubes (PMT) voltages, electrical charge rings, gates for cell sorting experiments, voltages applied to plates, and flow rates. In some aspects, gating may involve selecting regions (e.g., defining a polygon region of a 2D plot, such as a scatter or intensity plot), wherein each region corresponds to a particular cell type. These regions may help establish configuration settings with which to collect each of these respective cell populations. The system may make adjustments to the configuration settings as the sorting experiment proceeds.

Scientific/clinical literature 46 may include information from the literature, lab protocols, FACS facilities, or databases that corresponds to flow cytometry configuration settings for various types of cells and/or types of flow cytometry experiments. For example, configuration settings may include voltage configuration settings for photomultiplier tubes (PMTs), plate voltages, electrical charge rings, cell types, gating configuration settings, flow rate configuration settings, fluorescent labels, etc. for a particular flow cytometry experiment involving a particular type of cell. Configuration settings 48 may include experimentally determined configuration settings for sorting cells by flow cytometry system 50.

Cell analytics sorting system 15 may include one or more modules or units to perform the various functions of present invention embodiments described herein. The various modules (e.g., NLP module 70, machine learning sorting module 72, cell sorting analytics module 74, ranked configuration settings module 76, cell sorting error module 77, etc.) may be implemented by any combination of any quantity of software and/or hardware modules or units, and may reside within memory 17, 23 of the server and/or client systems for execution by processor 16, 22. In some cases, the cell analytics sorting system 15 may reside within the flow cytometry system 50 or may be on a separate computing device (e.g., server systems 10) in communication with the flow cytometry system 50, to automatically configure the flow cytometry system. The cell analytics sorting system 15 may automatically determine configuration settings prior to a sorting experiment and may automatically adjust the configuration settings of the flow cytometry system as the sorting experiment progresses.

Once the sorting experiment is underway, the flow cytometry system 50 may provide feedback to the cell analytics sorting system 15 to improve sorting. For example, if cells are not sufficiently separated into a single stream, the cell analytics sorting system 15 may adjust the configuration settings (e.g., flow rate) and provide the updated configuration settings to the flow cytometry system 50. As another example, if cells are not sorted properly, gating may be adjusted. In some aspects, these techniques may be integrated with current flow cytometry systems, and machine learning may be applied to adjust the flow rate, PMT voltages, detector voltages, plate voltages, electrical charging ring voltages, and/or gating to adapt and optimize flow cytometry configuration settings to specific cell populations in real or quasi-real time.

Natural language processing (NLP) module 70 extracts information from scientific/clinical literature 46, which may include but is not limited to research publications, clinical trial information, laboratory procedures and protocols, review articles, pathology guides, scientific literature, information from research institutions/clinical facilities, or any other scientific source of information that may be analyzed by NLP module 70. In general, the articles will be machine readable. Types of sorting experiments, expected sorting results, and configuration settings available in cytometry protocols and in the scientific literature may be mined using NLP and other similar approaches.

NLP module 70 may also extract other features from scientific/clinical literature 46, including but not limited to morphological features of respective types of cells (e.g., cell size (e.g., from 0.5 µM to 100 µm), cell shape, cell radius, cell appearance, cell diameter, presence and intensity of biomarker(s), etc.) from flow cytometry experiments. NLP module 70 may be used to extract information on biomarkers used to label different cell types.

From this extracted information, machine learning training data 42 may be generated to train the machine learning sorting module 72 to select configuration settings before (e.g., during set up) and during sorting experiments. In some aspects, the data for training the machine learning module 72 is obtained from the above referenced sources and may be validated by subject matter experts.

Machine learning sorting module 72, once trained, may be used to automatically select and adjust configuration settings associated with flow cytometry system 50, including PMT voltages, the type of sorting experiment, flow rates, detector voltages, gating, biomarkers, and other cell characteristics. In some aspects, the machine learning system may consider the specific type of flow cytometry system, given that different flow cytometry systems may comprise different components with different characteristics, and therefore, configurations settings may be optimized on a system-by-system basis.

Machine learning sorting module 72 may use any suitable machine learning technique, including but not limited to statistical classification, supervised learning, unsupervised learning, artificial neural networks, deep learning neural networks, cluster analysis, random forest, dimensionality reduction, binary classification, decision tree, etc. to select configuration settings and to adjust configuration settings during cell sorting.

Machine learning sorting module 72 may also analyze historical information of cell sorting to determine configuration settings from various data sources (e.g., unpublished experiments, publications, lab protocols, academic and clinical facilities, previous sorting experiments using flow cytometry system 50, etc.), and may automatically provide configuration settings to configure a cytometry device (e.g., a FACS machine) for a desired sorting experiment. In other aspects, machine learning sorting module 72 may identify potential configuration errors, and may suggest modifications to a predetermined configuration or may provide a new configuration to the flow cytometry system 50. Reconfiguration may be performed at the start of a sorting experiment or during a sorting experiment to correct the configuration error. In some cases, the system may identify damaged cells or debris, and may exclude these components from cytometry analysis, with such components directed to a fraction that is discarded during cell collection.

Cell sorting analytics module 74 may classify the cells into respective categories based upon forward scatter and side scatter and/or fluorescence of a labeled cell. Gating may be determined based upon the classification, in some cases, by the cell sorting analytics module 74. Once gating has been performed, characteristics may be defined with which to collect cells. For example, the flow cytometry system may charge a droplet containing a cell, wherein the cell has a side scatter and forward scatter or other characteristic such as fluorescent intensity falling within a gated area, and may apply a voltage to plates to deflect the charged cell into a corresponding receiving container for cell collection. Sorting of cells may be based on various properties, including but not limited to cell shape, cell size, intensity of fluorescent label, density of the sample, etc. as determined by forward and side scatter techniques, as well as the intensity of one or more fluorescent tags.

Ranked configuration settings module 76 may return a list of sets of configuration settings for a given cell type and/or type of experiment. The system may rank the configuration settings according to optimal sorting results (e.g., based on recovery, purity, etc. with regard to cell sorting). In some cases, the flow cytometry system may start the cell sorting experiment with the top ranked set of configuration settings, and may alter the configuration settings (e.g., to select the second ranked set, or the third ranked set, etc.) by selecting a different set in the ranked list to optimize cell sorting.

Cell sorting error module 77 evaluates cell sorting results to determine experimental error. Techniques for determining error in flow cytometry/FCAS are known in the art. The experimental error may be provided as feedback to the biological cell analysis sorting machine, and the configuration settings may be modified automatically to reduce experimental error. In this case, real-time or near real-time evaluation of experimental error may be provided as feedback to the biological cell analysis sorting machine, which modifies the configuration settings until cell sorting results are improved.

Flow cytometry system 50 comprises a cell suspension 51, an ultrasonic nozzle 52 for creating droplets (each droplet preferably containing a single cell), a laser 54, a detector 55, an analyzer 56, voltage plates 57, containers 58 for cells, electrical charging ring 59, and corresponding tubing (not shown). A suspension of cells may be placed in a reservoir. A stream of fluid from the reservoir may join a sheath flow (a saline-based fluid without cells) in order to form a stream comprising single cells. The stream of cells may be contacted with a laser, with light scatter or fluorescence intensity detected by the detectors (PMTs) and provided to the analyzer. The detectors detect light scatter or fluorescence intensity from the laser interactions with the cells, and this information may be used to generate scatter plots (e.g., forward scatter and side scatter plots), which may be used for gating cells.

The analyzer may analyze forward and side light scatter or intensity of fluorescent cells and this information may be provided to cell sorting analytics module 74 for gating.

Forward scatter is proportional to the size of the cell (e.g., with smaller cells having smaller forward scatter and larger cells having larger forward scatter), and may be converted into a voltage signal proportional to the amount of forward scattered light. Side scatter is proportional to the shape and internal granularity and complexity of the cell, and may be converted into a voltage signal proportional to the amount of side scattered light. The detector for forward scatter may be in-line with the laser, while the detector for side scatter is perpendicular to the laser. In some cases, the forward scatter and side scatter voltages for each cell may be plotted respectively on an x and y axis to generate a scatter plot. Typically, groups of cells with different characteristics will appear as clusters on the scatter plot. Polygons may be drawn around these clusters, in a process known as gating to select features (e.g., ranges of light or intensity scatter) with which to collect cells.

Fluorescence-activated cell sorting (FACS) is a subcategory of flow cytometry. Fluorescent molecules (e.g., fluorescent labeled antibodies) may be used to tag cells. When contacted with a laser, the fluorophore may be excited to a higher energy level. The fluorophore returns to the ground energy state and emits light corresponding to a specific wavelength. The emitted light follows the same path as side scattered light, traveling through filters and mirrors, to direct wavelength ranges of light to detectors (e.g., PMTs). The fluorescence can be converted into a corresponding voltage, wherein the magnitude of the voltage corresponds to the intensity of the fluorescence.

For cell collection, once gating has been performed, the stream may pass through the ultrasonic nozzle to form droplets of single cells. The droplets may pass through an electrical charging ring in order to be charged, positively or negatively. Cells that are to be collected fall within a gating region and are charged, while cells outside of the gating regions are not charged and flow to the waste contained. In FACS, cells may be charged in proportion to their fluorescent intensity. The charged droplets pass through plates to which a voltage is applied, e.g., two plates, one having a negative charge and the other having a positive charge. The positively charged cells are directed to the negatively charged plate and the negatively charged cells are directed to the positively charged plate. Accordingly, the trajectory of the cell can be altered, such that the cell is directed to a specific collection tube, based upon the magnitude of the deflection.

Figure 2:
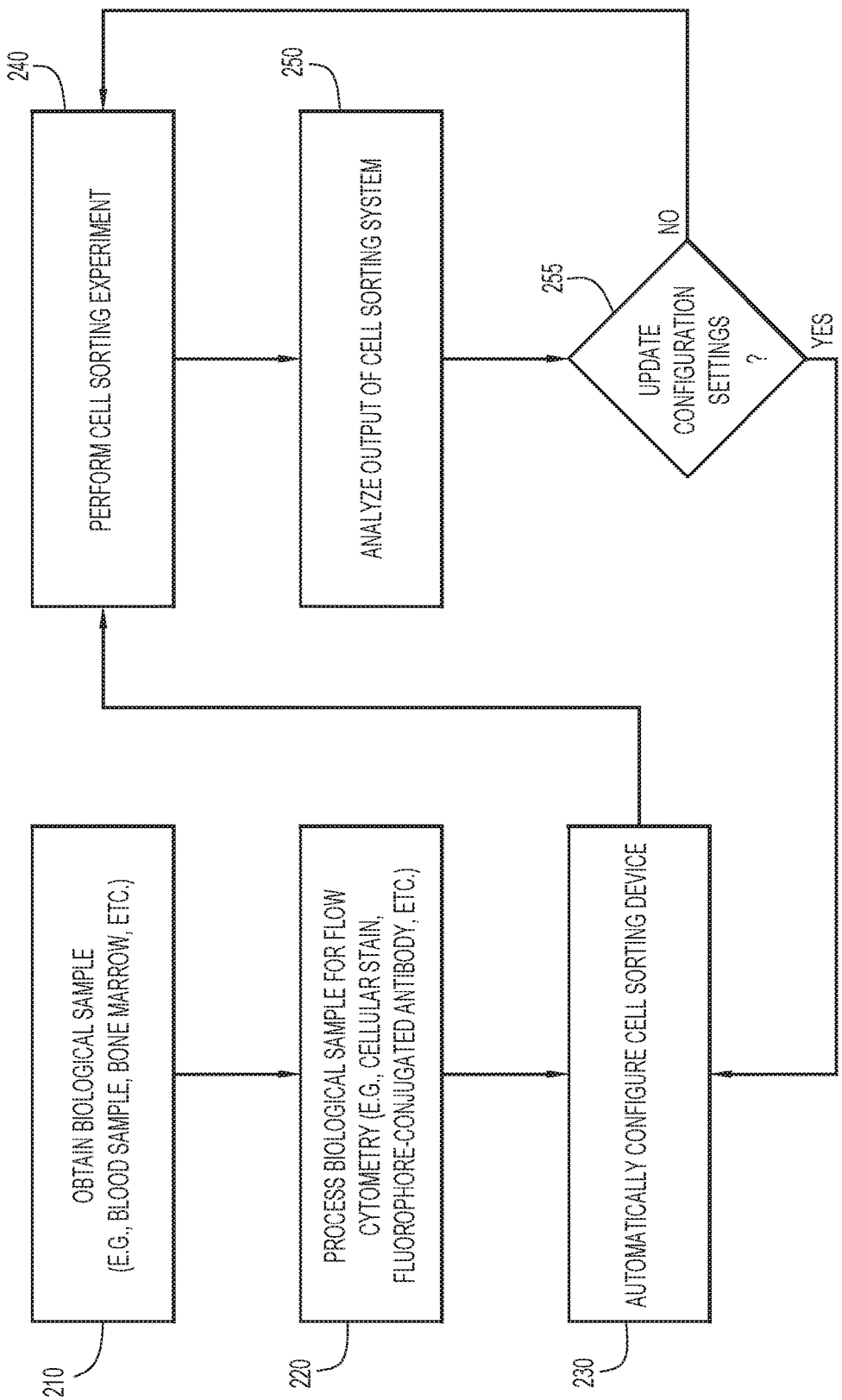
FIG. 2 is a flow diagram showing an overview of cell sorting operations, according to embodiments of the present disclosure.

FIG. 2 is a flow diagram showing determination of and adaptive application of flow cytometry configuration settings. At operation 210, a biological sample is obtained. At operation 220, the biological sample is processed for flow cytometry. Processing may include staining/dyes, labeling with a fluorophore conjugated antibody, purification, etc. At operation 230, the cell sorting device is configured automatically, with predetermined configuration settings for a given cell type and type of sorting experiment. At operation 240, the cell sorting experiment is performed. At operation 250, the output of the cell analytics sorting system is analyzed to determine purity of cell sorting. If the results do not meet a specified threshold (e.g., achieving a suitable level of purity), the machine learning system may suggest updated configuration settings to improve sorting, at operation 255. If the configuration settings are updated, due to the output of the cell analytics sorting system being below an acceptable threshold (e.g., for single cells in a droplet, for achieving a suitable level of cell sorting with regard to contamination, etc.), the flow cytometry system will implement the updated configuration settings, and the sorting experiment will proceed with the updated configuration settings at operation 230. If the sorting experiment is proceeding according to desired results, the configuration settings will not be updated, and the sorting experiment may continue at operation 240 while undergoing further monitoring and analysis at operation 250.

Figure 3:
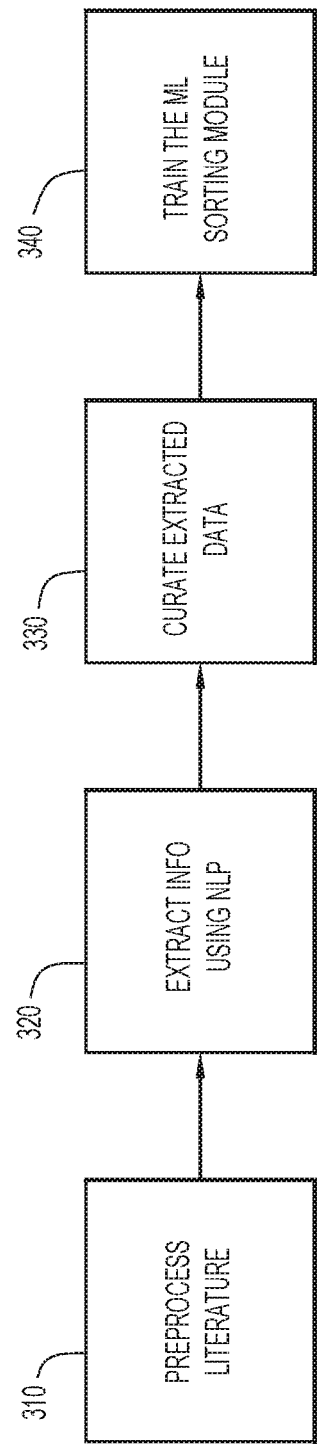
FIG. 3 is a flow diagram showing extraction and generation of training data for machine learning module of the biological cell analysis sorting machine, according to embodiments of the present disclosure.

FIG. 3 shows a flow chart for generation of training data for the machine learning sorting module 72. At operation 310, literature and other information 46 are pre-processed to be machine readable (e.g., by optical character recognition, etc.). The literature may include but is not limited to scientific publications, clinical reports, internal company information, experimental protocols, databases, abstracts, conference proceedings, etc. At operation 320, NLP module 72 may be used to extract information pertaining to configuration settings for flow cytometry for a given cell type suitable for generating a training data set. These configuration settings may include flow rates, voltages of the PMTs, plate voltages, number of collection tubes, cell types, cell labeling, type of sorting experiment, etc. Any suitable cell type may be included, including blood cells and other cells present in the circulating blood (e.g., white blood cells such as monocytes, lymphocytes, basophils, eosinophils, granulocytes, natural killer cells, T cells, red blood cells, cancer cells, epithelial cells, or other cells present in a blood sample at a low concentration (cancer cells), etc.). At operation 330, the extracted information may be curated and/or annotated prior to providing to the machine learning sorting module. For example, the extracted data may be curated by a subject matter expert, such as a flow cytometry expert or scientist with expertise in configuring FACS machines for cell sorting. The curated and/or annotated data may be provided to the machine learning sorting module 72 as training data 42, and the machine learning sorting module may be trained at operation 340. In some aspects, the training data may include a cell type (e.g., including cell size, cell shape, other cell properties, etc.) along with cytometry configuration settings including the type of stain or label used to visualize the cell along with flow rates, voltages of the PMTs, gates, plate voltages, electrical charging ring voltages, type of sorting experiment, etc. The training data is provided to the cell analytics sorting system 15 to train the machine learning sorting module 72 to sort a cell sample into respective components.

Once trained, machine learning sorting module 72 can automatically select conditions for a cell sorting experiment and may use this information to configure flow cytometry system 50. By applying machine learning to the flow cytometry system, conditions may be adapted to specific cell populations in real time or in quasi-real time. The present techniques may also provide feedback from flow cytometry experiments to cell analytics sorting system 15 to detect and flag potential issues from analyzing and sorting a given sample containing a mixture of cell populations.

The present flow cytometry system is not limited to sorting and analyzing a mixture of positive and negatively charged cells for one biomarker. The system may be trained to simultaneously sort cells based on multiple biomarkers depending upon the experiment, for instance, two to six biomarkers for cell proliferation, two to six biomarkers for immunophenotyping, or more (e.g., two to eighteen different fluorescent markers), etc. Thus, the present techniques may sort cells based on any suitable feature, including one or more biomarkers.

The cell analytics sorting system may analyze sorting experiments and provide recommendations and analysis pertaining to the sorting experiment. For example, the cell analytics sorting system may identify potentially failed experiments (e.g., by identifying user configurations that are substantially different from machine learning generated configuration settings, etc.). In addition, the system may provide experimental conclusions based on the presence and frequency of the different cell populations (e.g., by analyzing light or fluorescence intensity scatter plots to determine whether a sufficient level of separation for a given cell type is reached). Additionally, the cell analytics sorting system may analyze different types of sorting experiments to determine results including but not limited to proliferation studies, viability studies, or immunophenotyping studies, e.g., from blood samples. For example, for a proliferation sorting experiment, a population of cells exposed to conditions to promote cell proliferation may be evaluated as compared to a control population. For an inhibition experiment, a population of cells exposed to an inhibitor may be evaluated as compared to a control population. For a viability experiment, a population of cells exposed to conditions to promote viability may be evaluated as compared to a control population.

Figure 4:
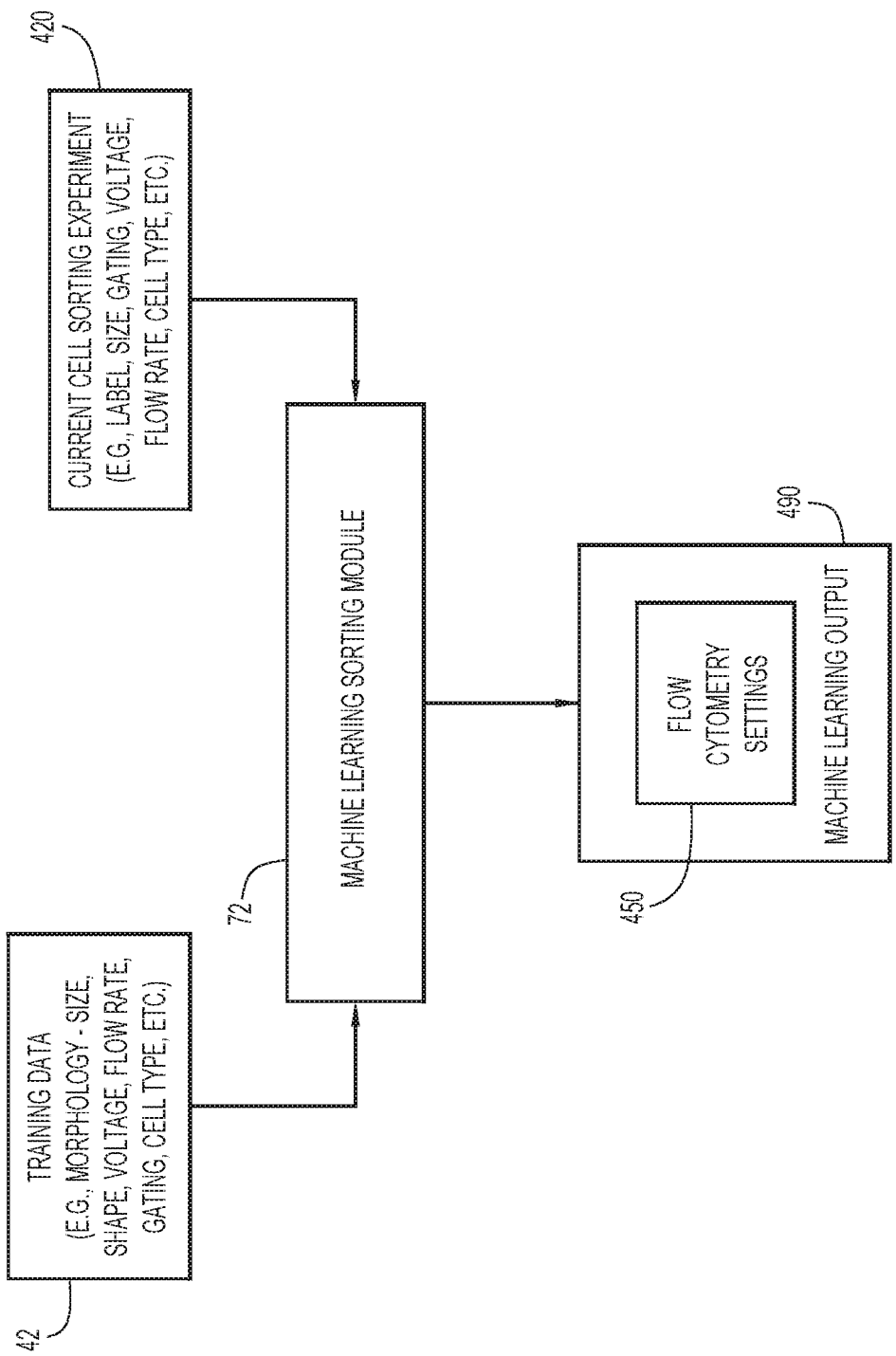
FIG. 4 is a diagram showing inputs and outputs of the machine learning system of the biological cell analysis sorting machine, according to embodiments of the present disclosure.

FIG. 4 shows a flowchart of inputs and outputs to machine learning sorting module 72. A machine learning process may be used to automatically and dynamically adjust FACS configuration settings, e.g., such as gating, flow rates, various voltages, etc. as well as other alignment and calibration configuration settings, during sorting in real time or quasi-real time to reach optimal or improved conditions. Machine learning sorting module 72 may comprise a plurality of sorting models, with a particular machine learning algorithm, specific to particular cell types, particular biological assays, and one or more biomarkers. As previously discussed, training data 42 may be provided to the machine learning module in order to train the respective machine learning model (e.g., for particular cell type(s)) to identify and sort cells from a biological sample, such as a blood sample. Output 490 of the machine learning sorting module may include various flow cytometry configuration settings 450.

Once the machine learning sorting module is trained, it may provide or analyze configuration settings for similar sorting assays. For current cell sorting experiments 420, the machine learning sorting module may provide updated configuration settings based on the type of cell, cell size, biolabel(s), and type of sorting experiment, PMT voltages, plate voltages, flow rates, gating, electrical charge ring voltages, cell characteristics, etc. In particular, the machine learning system may provide parameters for a sorting experiment, including PMT voltages, electrical charge ring voltages, flow rates, and plate voltages. Additionally, the machine learning system may determine gating, identifying areas around particular populations of cells from 2D scatter or intensity plots, which may be used to collect the cells. If the updated settings are different from the current configuration settings, the cell analytics sorting system may notify the user of a possible configuration error, and the user may have the option of adjusting the configuration settings. Alternatively, the system may automatically select an updated set of configuration settings and may provide the configuration settings to the flow cytometry system.

A blood sample may comprise a variety of cell types, including but not limited to normal red blood cells, abnormal red blood cells, white blood cells (including granulocytes/polymorphonuclear leukocytes (e.g., neutrophils, eosinophils, basophils, etc.), mononuclear leukocytes (lymphocytes, monocytes, etc.)), and other cells (e.g., circulating cancer/tumor cells, epithelial cells, etc.). The system may be used to sort these cell types as well as cultured cells (e.g., cells frown in a laboratory for research purposes, mammalian cells, cells from tissue samples, etc.). Alternatively, the system may be used to sort cells from tissue samples that have been cultured or subjected to resuspension.

Figure 5:
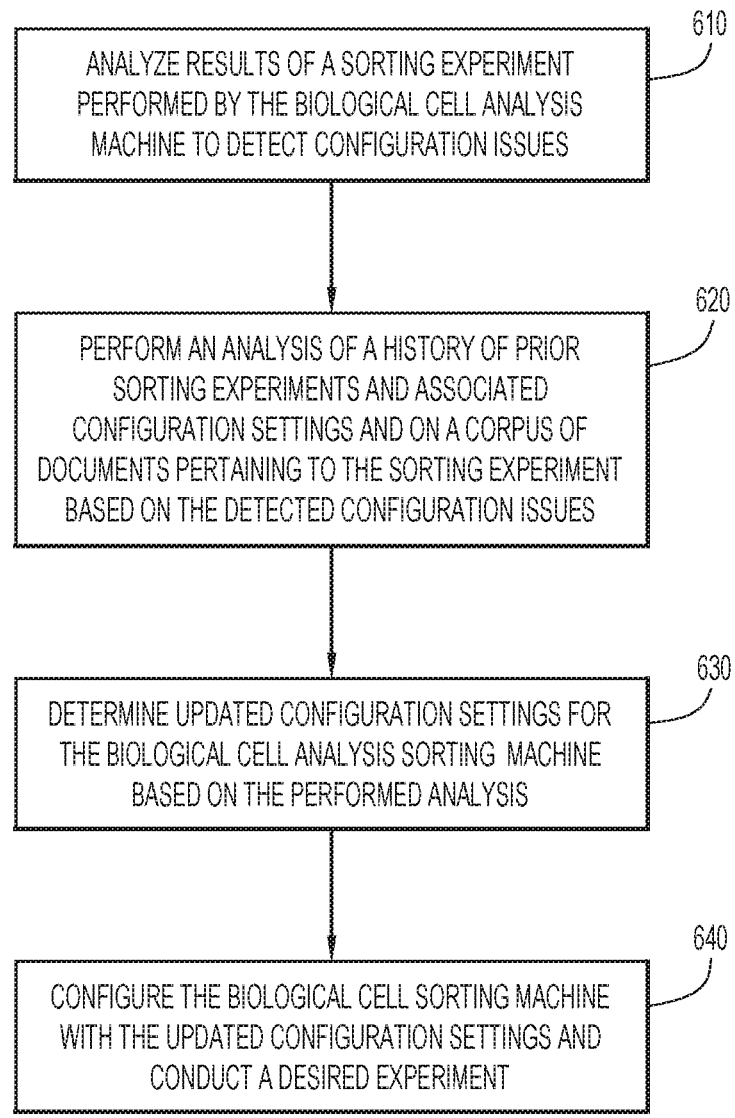
FIG. 5 is a high level flow diagram of the biological cell analysis sorting machine, according to embodiments of the present disclosure.

FIG. 5 shows a flow chart of example operations for using machine learning to sort cells. At operation 610, results of a sorting experiment performed by the biological cell analysis sorting machine are analyzed to detect configuration issues. At operation 620, a history of prior sorting experiments and associated configuration settings and a corpus of documents pertaining to the sorting experiment are analyzed based on the detected configuration issues. At operation 630, updated configuration settings are determined for the biological cell analysis sorting machine based on the performed analysis. At operation 640, the biological cell sorting machine is configured with the updated configuration settings and a desired experiment is conducted.

Present techniques provide a variety of advantages over existing approaches. These approaches speed up, simplify, and improve robustness of flow cytometry techniques for immunophenotyping and other types of experiments.

Advantages include using a machine learning process to automatically configure FACS configuration settings, such as gates, flow rates, various voltages, etc. as well as other alignment and calibration configuration settings. The machine learning process may be used to automatically and dynamically adjust FACS configuration settings during sorting in real time or quasi-real time to reach optimal or improved conditions. Particular FACS machine learning models may be generated and used to sort particular cell types for particular biological assays, and the FACS machine learning models may be trained on multiple biomarkers. Present techniques improve reproducibility of flow cytometry experiments, and automate aspects of this process.

It will be appreciated that the embodiments described above and illustrated in the drawings represent only a few of the many ways of implementing embodiments for automating flow cytometry/FACS techniques.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, document filtration system, etc.). These systems may include any types of monitors and input devices (e.g., keyboard, mouse, voice recognition, etc.) to enter and/or view information.

It is to be understood that the software (e.g., cell analytics sorting system 15, including NLP module 70, machine learning sorting module 72, cell sorting analytics module 74, ranked configuration settings module 76, cell sorting error module 77, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., cell analytics sorting system 15, including NLP module 70, machine learning sorting module 72, cell sorting analytics module 74, ranked configuration settings module 76, cell sorting error module 77, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., machine learning training data 42, scientific clinical literature 46, configuration settings 48, etc.). The database system may be implemented by any number of any conventional or other databases, data stores or storage structures (e.g., files, databases, data structures, data or other repositories, etc.) to store information (e.g., machine learning training data 42, scientific clinical literature 46, configuration settings 48, etc.). The database system may be included within or coupled to the server and/or client systems. The database systems and/or storage structures may be remote from or local to the computer or other processing systems, and may store any desired data (e.g., machine learning training data 42, scientific clinical literature 46, configuration settings 48, etc.).

The present invention embodiments may employ any number of any type of user interface (e.g., Graphical User Interface (GUI), command-line, prompt, etc.) for obtaining or providing information (e.g., machine learning training data 42, scientific clinical literature 46, configuration settings 48, etc.), where the interface may include any information arranged in any fashion. The interface may include any number of any types of input or actuation mechanisms (e.g., buttons, icons, fields, boxes, links, etc.) disposed at any location to enter/display information and initiate desired actions via any suitable input devices (e.g., mouse, keyboard, etc.). The interface screens may include any suitable actuators (e.g., links, tabs, etc.) to navigate between the screens in any fashion.

The report may include a listing of prioritized configuration settings along with any other information arranged in any fashion, and may be configurable based on rules or other criteria to provide desired information to a user (e.g., flow cytometry analytics, ranked configuration settings, error analysis, etc.).

The present invention embodiments are not limited to the specific tasks or algorithms described above, but may be utilized for any application in which sorting cells using flow cytometry/FACS is being performed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises a document of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of configuring a biological cell analysis sorting machine, wherein the biological cell analysis sorting machine comprises a flow cytometry system and a cell analytics sorting system, for conducting a sorting experiment comprising:
    analyzing results of a sorting experiment performed by the biological cell analysis sorting machine to detect configuration issues;
    performing an analysis of historical data of prior sorting experiments and associated configuration settings extracted from a corpus of documents pertaining to the sorting experiment based on the detected configuration issues;
    determining updated configuration settings for the biological cell analysis sorting machine based on the performed analysis, wherein the updated configuration settings are determined using a machine learning system, wherein the machine learning system is trained using configuration settings extracted from the historical data of the prior sorting experiments;
    configuring the biological cell analysis sorting machine, during a desired experiment, with the updated configuration settings and conducting the desired experiment;
    providing a list of alternative updated configuration settings by the machine learning system, wherein the list of alternative updated configuration settings includes gating configuration settings that indicate one or more areas corresponding to gating of cells, wherein each area corresponds to a particular cell type;
    ranking the updated alternative configuration settings for the flow cytometry system based on a predicted cell sorting efficiency for collected cell types; and
    when the cell sorting efficiency is not achieved, implementing an alternative ranked updated configuration setting selected from the list of alternative updated configuration settings until the cell sorting efficiency is achieved.

2. The method of claim 1, wherein the one or more areas corresponding to gating of cells each comprise a polygon region of a two-dimensional scatter plot or two-dimensional intensity plot.

3. The method of claim 1, wherein the updated configuration settings are selected based upon a cell type.

4. The method of claim 1, further comprising:
    evaluating cell sorting results based upon a determined experimental error;
    providing the experimental error as feedback to the biological cell analysis sorting machine; and
    modifying the configuration settings to reduce the experimental error.

5. The method of claim 1, wherein the biological cell analysis sorting machine is configured to sort cells based on the presence of two to six biomarkers.

6. The method of claim 1, wherein the historical data comprises flow cytometry sorting experiments from one or more from a group of scientific literature, lab protocols, academic institutions, research institutions, and previously conducted sorting experiments by the flow cytometry system.

7. A system for configuring a biological cell analysis sorting machine, wherein the biological cell analysis sorting machine comprises a flow cytometry system and a cell analytics sorting system for conducting a sorting experiment, the system comprising at least one processor configured to:
    analyze results of a sorting experiment performed by the biological cell analysis sorting machine to detect configuration issues;
    perform an analysis of historical data of prior sorting experiments and associated configuration settings extracted from a corpus of documents pertaining to the sorting experiment based on the detected configuration issues;
    determine updated configuration settings for the biological cell analysis sorting machine based on the performed analysis, wherein the updated configuration settings are determined using a machine learning system, wherein the machine learning system is trained using configuration settings extracted from the historical data of the prior sorting experiments;
    configure the biological cell analysis sorting machine, during a desired experiment, with the updated configuration settings and conduct the desired experiment;
    provide a list of alternative updated configuration settings by the machine learning system, wherein the list of alternative updated configuration settings includes gating configuration settings that indicate one or more areas corresponding to gating of cells, wherein each area corresponds to a particular cell type;

rank the updated alternative configuration settings for the flow cytometry system based on a predicted cell sorting efficiency for collected cell types; and when the cell sorting efficiency is not achieved, implement an alternative ranked updated configuration setting selected from the list of alternative updated configuration settings until the cell sorting efficiency is achieved.

8. The system of claim 7, wherein the one or more areas corresponding to gating of cells each comprise a polygon region of a two-dimensional scatter plot or two-dimensional intensity plot.

9. The system of claim 7, wherein the updated configuration settings are selected based upon a cell type.

10. The system of claim 7, wherein the at least one processor is further configured to:

evaluate cell sorting results based upon a determined experimental error;

provide the experimental error as feedback to the biological cell analysis sorting machine; and modify the configuration settings to reduce the experimental error.

11. The system of claim 7, wherein the biological cell analysis sorting machine is configured to sort cells based on the presence of two to six biomarkers.

12. The system of claim 7, wherein the historical data comprises flow cytometry sorting experiments from one or more from a group of scientific literature, lab protocols, academic institutions, research institutions, and previously conducted sorting experiments by the flow cytometry system.

13. A computer program product for configuring a biological cell analysis sorting machine, wherein the biological cell analysis sorting machine comprises a flow cytometry system and a cell analytics sorting system for conducting a sorting experiment, the computer program product comprising one or more computer readable storage media collectively having program instructions embodied therewith, the program instructions executable by a computer to cause the computer to:

analyze results of a sorting experiment performed by the biological cell analysis sorting machine to detect configuration issues;

perform an analysis of historical data of prior sorting experiments and associated configuration settings extracted from a corpus of documents pertaining to the sorting experiment based on the detected configuration issues;

determine updated configuration settings for the biological cell analysis sorting machine based on the performed analysis, wherein the updated configuration settings are determined using a machine learning system, wherein the machine learning system is trained using configuration settings extracted from the historical data of the prior sorting experiments;

configure the biological cell analysis sorting machine, during a desired experiment, with the updated configuration settings and conduct the desired experiment;

provide a list of alternative updated configuration settings by the machine learning system, wherein the list of alternative updated configuration settings includes gating configuration settings that indicate one or more areas corresponding to gating of cells, wherein each area corresponds to a particular cell type;

rank the updated alternative configuration settings for the flow cytometry system based on a predicted cell sorting efficiency for collected cell types; and when the cell sorting efficiency is not achieved, implement an alternative ranked updated configuration setting selected from the list of alternative updated configuration settings until the cell sorting efficiency is achieved.

14. The computer program product of claim 13, wherein the one or more areas corresponding to gating of cells each comprise a polygon region of a two-dimensional scatter plot or two-dimensional intensity plot.

* * * * *